United States Patent [19]
Wassell

[11] Patent Number: 4,935,965
[45] Date of Patent: Jun. 26, 1990

[54] EAR MUFF

[76] Inventor: Stephen R. Wassell, 8542 Mt. Vernon Hwy., Alexandria, Va. 22309

[21] Appl. No.: 257,871

[22] Filed: Oct. 14, 1988

[51] Int. Cl.⁵ .............................................. A41D 21/00
[52] U.S. Cl. ......................................... 2/209; 181/129
[58] Field of Search .................... 2/209, 174; 128/866; 181/129

[56]  References Cited
U.S. PATENT DOCUMENTS

| | | | |
|---|---|---|---|
| 1,468,556 | 9/1923 | Camp et al. | 2/209 UX |
| 2,700,162 | 1/1955 | Fuller | 2/209 |
| 3,354,471 | 12/1967 | Longo | 2/209 X |
| 4,616,643 | 10/1986 | Jung | 2/209 X |
| 4,660,229 | 4/1987 | Harris | 2/209 |
| 4,791,684 | 12/1988 | Schwartz | 2/209 |

Primary Examiner—Peter Nerbun

[57] ABSTRACT

The ear muff according to the present invention is a water-repellent material lined with thin insulation sewn into the form of a pocket which fits around the ear of the wearer to protect the ear against cold, wind, snow, or the like without substantially impairing hearing. The ear muff is kept engaged to the ear by means of an elastic loop residing in the hem of the opening of the pocket which contracts around the base of the ear, and in addition, adjacent to the elastic within the hem, a malleable earlobe clasp which the wearer clamps around the earlobe, so that the ear muff can be used by people with attached earlobes as well as by people with unattached earlobes. The lined water-repellent material comprising the pocket plays no part in keeping the ear muff engaged to the ear, and thus is made of flexible material so that it can conform to various shapes of ears.

1 Claim, 1 Drawing Sheet

U.S. Patent     Jun. 26, 1990     4,935,965
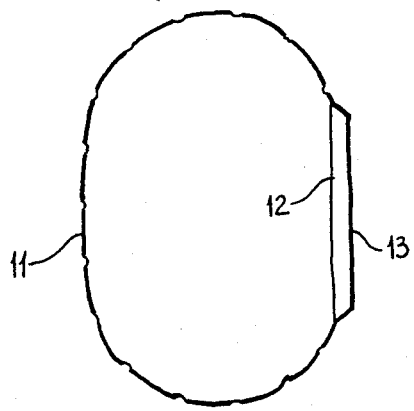
FIGURE 1
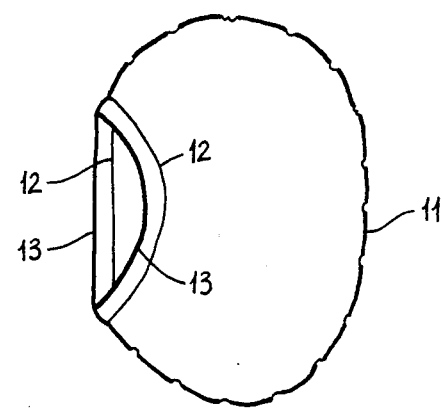
FIGURE 2
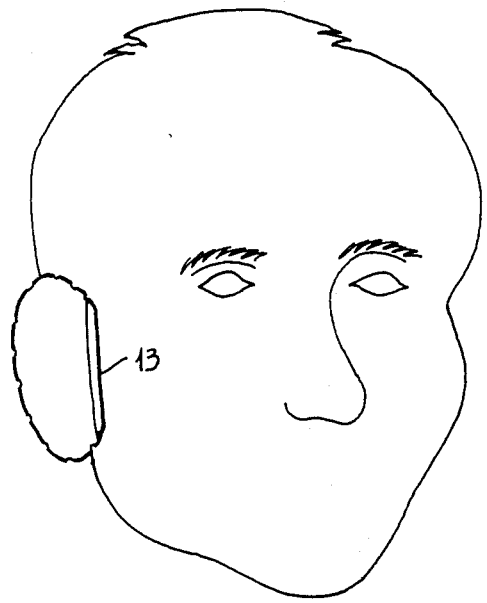
FIGURE 3
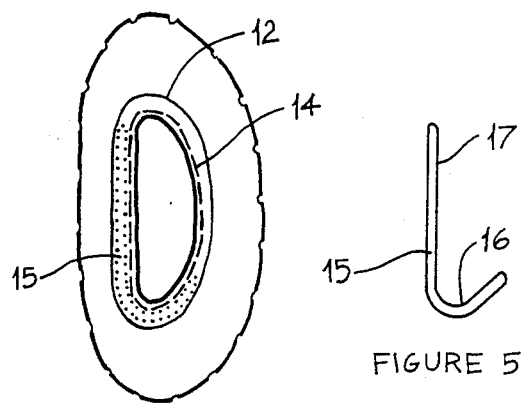
FIGURE 4
FIGURE 5
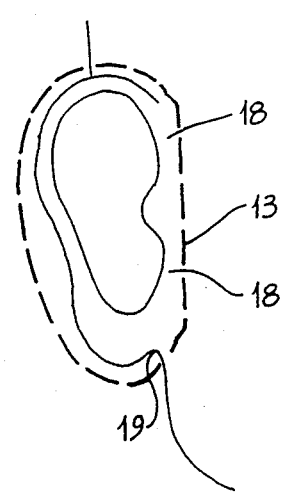
FIGURE 6
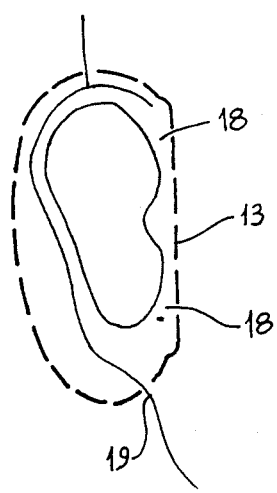
FIGURE 7

EAR MUFF

This invention relates to ear muffs that are used to protect the ears of the wearer against cold, wind, snow, or the like, specifically to earheld ear muffs, which do not have a band extending over the head to keep the ear muffs engaged to the ears of the wearer.

Each previously patented earheld ear muff has been designed to maintain a certain shape in order to stay on the ear, impairing comfort for most people and impairing fit for people with unusually shaped ears. In addition, most of the previously designed ear muffs have been rigid and/or heavy, further impairing fit and comfort.

Therefore, it is an object of the present invention to provide an improved, earheld ear muff which is made of a thin, water-repellent outer shell and a thin, insulating inner lining so that the ear muff will comfortably keep the ears warm and dry during outdoor winter activities without substantially impairing hearing.

A further object of the present invention is to provide an ear muff which is equally usable by wearers who have attached earlobes as well as by wearers who have unattached earlobes, attached earlobes being earlobes which blend directly into the head rather than curving upwards to meet the head, as further described below.

A further object of the present invention is to provide an ear muff which will stay securely engaged to the ear of the wearer even during such rigorous activities as skiing, regardless of the anatomical features of the wearer's ear.

The ear muff according to the present invention is illustrated in the accompanying drawing in which:

FIG. 1 shows the front view of the ear muff for the right ear.

FIG. 2 shows the rear view of the ear muff for the right ear.

FIG. 3 shows the ear muff as applied to the ear of the wearer; the head of the wearer is shown merely for purpose of illustration.

FIG. 4 shows the side view of the ear muff for the right ear.

FIG. 5 shows the shape of the earlobe clasp.

FIG. 6 shows an ear with unattached earlobes.

FIG. 7 shows an ear with attached earlobes.

The ear muff according to the present invention is constructed from two pieces of a thin, flexible, water-repellent outer shell and two matching pieces of thin, flexible, insulating lining. As shown in FIGS. 1 and 2, the material is sewn together, with the water-repellent shell on the exterior, to form an approximately oval pocket of material with an opening on one side. There is a seam around the outer edge 11, and a continuous hem 12 around the opening 13. As shown in FIG. 3, the pocket is designed to receive the ear of the wearer within its opening, so that the ear muff is pulled entirely around the ear with the opening 13 of the pocket engaged directly to the base of the ear, the base of the ear being the juncture between the ear and the head. The front ear base 18 and the earlobe base 19 are shown in FIGS. 6 and 7.

As shown in FIG. 4, the opening of the ear muff according to the present invention will be equipped with an endless loop of elastic 14 (dashed line) within its hem, so that the opening contracts around the base of the ear. In addition, the ear muff contains a malleable yet shape-holding earlobe clasp along with the elastic, residing adjacent to the elastic within the hem. As shown in FIG. 4, the earlobe clasp 15 (dotted line) will run the length of the front hem and will hook around the earlobe base. A side view of the earlobe clasp (before being bent by the wearer) is shown in FIG. 5.

The earlobe clasp helps the ear muff conform to the ear of the wearer in two ways. The first way the wearer uses the earlobe clasp is to clamp the hooked portion 16 of the earlobe clasp around his or her earlobe. This first use for the earlobe clasp is designed for wearers who have attached earlobes (see FIG. 7), as opposed to unattached earlobes (see FIG. 6), since clamping the earlobe clasp about the earlobe base will keep the opening of the ear muff from slipping up the ear. As opposed to previously patented earheld earmuffs which include some sort of earlobe clasp, such as Fuller's U.S. Pat. No. 2,700,162 or Longo's U.S. Pat. No. 3,354,471, the earlobe clasp according to the present invention is clamped onto the earlobe precisely where the most additional holding power is needed for people with attached earlobes. Specifically, this is precisely where the attached earlobe blends into the head at the earlobe base 19.

The second use for the earlobe clasp is to press the straight portion 17 of the earlobe clasp against the head directly in front of the ear so that the earlobe clasp will conform to the contour of the head directly in front of the ear. This will help keep a cold draft from leaking between the ear muff and the front ear base when the wearer is facing a head-on wind, as in skiing. This air leakage has not been addressed in any of the previously patented earheld ear muffs.

The combination of the elastic and the novel earlobe clasp will keep the ear muff in place around the ear of the wearer by keeping the opening of the pocket firmly engaged to the base of the ear. The material that actually envelopes the ear does not function to keep the ear muff engaged to the ear of the wearer. Therefore, this same material, consisting of the flexible outer shell and inner insulation, is free to conform to the shape of the wearer's ear to provide maximum fit and comfort.

The inventor claims:

1. An earheld ear muff which is constructed of a flexible sound-admitting water-repellent outer shell and a thin insulating inner lining sewn together in the form of a pocket with a hemmed opening on one side, which receives the ear of the wearer within the pocket so that the opening of the pocket is engaged to the base of the ear, which contains within a hem of the opening an endless loop of elastic so that the opening contracts to the base of the ear, which also contains within the hem of the opening an earlobe clasp that is used to clamp the opening about the earlobe of the wearer and to press the opening against the head of the wearer directly in front of the ear to keep the ear muff securely engaged to the ear of the wearer regardless of whether the wearer has attached earlobes or unattached earlobes, the hem including a lower section corresponding to the bottom of the wearer's ear and a forward section corresponding to the front of the wearer's ear, said earlobe clasp extending through said lower and forward sections of the hem, said ear muff being engaged to the ear by means of the elastic and earlobe clasp, so that the pocket itself, made of the flexible outer shell and inner lining, can conform to the shape of virtually any ear.

* * * * *